US009527793B2

(12) United States Patent
Anderson, Jr. et al.

(10) Patent No.: US 9,527,793 B2
(45) Date of Patent: Dec. 27, 2016

(54) MANDELIC ACID CONDENSATION POLYMERS

(71) Applicants: Rush University Medical Center, Chicago, IL (US); The Board of Trustees of the University of Illinois, Urbana, IL (US)

(72) Inventors: Robert A. Anderson, Jr., Chicago, IL (US); Xiao-Hui Diao, Chicago, IL (US); Lourens J. D. Zaneveld, Sao Paulo (BR); Calvin J. Chany, II, Dubuque, IA (US); Aleksej Krunic, Chicago, IL (US); Donald P. Waller, Oak Brook, IL (US); Duane L. Venton, Lombard, IL (US); Sanjay Jain, Pune (IN)

(73) Assignees: THE BOARD OF TRUSTEES OF THE UNIVERSITY OF ILLINOIS, Urbana, IL (US); RUSH UNIVERSITY MEDICAL CENTER, Chicago, IL (US)

( * ) Notice: Subject to any disclaimer, the term of this patent is extended or adjusted under 35 U.S.C. 154(b) by 0 days.

(21) Appl. No.: 14/361,993

(22) PCT Filed: Nov. 30, 2012

(86) PCT No.: PCT/US2012/067452
§ 371 (c)(1),
(2) Date: May 30, 2014

(87) PCT Pub. No.: WO2013/082533
PCT Pub. Date: Jun. 6, 2013

(65) Prior Publication Data
US 2014/0371310 A1 Dec. 18, 2014

Related U.S. Application Data

(60) Provisional application No. 61/566,441, filed on Dec. 2, 2011.

(51) Int. Cl.
C07C 59/50 (2006.01)
C07C 59/48 (2006.01)
C07C 51/347 (2006.01)
C07C 67/465 (2006.01)
C07C 69/616 (2006.01)

(52) U.S. Cl.
CPC ............ C07C 59/50 (2013.01); C07C 51/347 (2013.01); C07C 59/48 (2013.01); C07C 67/465 (2013.01); C07C 69/616 (2013.01); C07C 2101/16 (2013.01)

(58) Field of Classification Search
CPC .................................................. C07C 59/50
See application file for complete search history.

(56) References Cited

U.S. PATENT DOCUMENTS

| 5,925,621 | A  |   | 7/1999 | Zaneveld et al. |
| 5,932,619 | A  | * | 8/1999 | Zaneveld et al. ............. 514/570 |
| 6,028,115 | A  |   | 2/2000 | Zaneveld et al. |
| 6,239,182 | B1 |   | 5/2001 | Zaneveld et al. |

FOREIGN PATENT DOCUMENTS

| CN | 1431186 A * | 7/2003 |
| WO | WO 2007022082 A2 * | 2/2007 |
| WO | 2007/140941 | 12/2007 |

OTHER PUBLICATIONS

Machine Translation of Chinese Patent Document No. CN 1431186 A by Wang et al., obtained from http://www.google.com/patents/CN1431186A?cl=en on Feb. 9, 2015.*
Ward et al. Biomacromolecules 2007, 8, 3308-3316.*
Zaneveld, et al., "Use of mandelic acid condensation polymer (SAMMA), a new antimicrobial contraceptive agent, for vaginal prophylaxis," Fertility and Sterility, 2002, vol. 78, No. 5, pp. 1107-1115.
Herold, B.C. et al., "Mandelic Acid Condensation Polymer: Novel Candidate Microbicide for Prevention of Human Immunodeficiency Virus and Herpes Simplex Virus Entry" Journal of Viology, 2002, vol. 76, No. 22, pp. 11236-11244.
PCT International Search Report and Written Opinion for Application No. PCT/US2012/067452 dated Mar. 25, 2013 (5 pages).
Ward, et al., "Anti-HIV-1 Activity of Poly(mandelic acid) Derivatives" Biomacromolecules, 2007, vol. 8, pp. 3308-3316.
Chang, T.L, et al., "SAMMA, a mandelic acid condensation polymer, inhibits dendritic cell-mediated HIV transmission." FEB (Federation of European Biochemical Societies), 2007. 581: p. 4596-4602.
Cheshenko, N., et al., "Candidate Topical Microbicides Bind Herpes Simplex Virus Glycoprotein B and Prevent Viral Entry and Cell-to-Cell Spread." Antimicrob Agent Chemother, 2004. 48: p. 2025-2036.
Anderson, R.A., et al., "SAMMA induces premature human acrosomal loss by Ca2+ signaling dysregulation." J. Androl., 2006. 27: p. 568-577.
Klebanoff, S.J. and R.W. Coombs, "Viricidal effect of Lactobacillus acidophilus on human immunodeficiency virus type-1: Possible role in heterosexual transmission." J Exp Med, 1991. 174: p. 289-292.
Zaneveld, L.J.D., et al., "Efficacy and safety of a new vaginal contraceptive antimicrobial formulation containing high molecular weight poly(4-styrenesulfonate)." Biol. Reprod., 2002. 66: p. 886-894.
UNAIDS. 2002. "Update report on the global HIV/AIDS epidemic, Dec. 2002." United Nations, Geneva, Switzerland.
Mauck, C.; Rosenberg, et al., "Recommendations for the clinical development of topical microbicides: an update." AIDS 2001, 15, 857-868.

(Continued)

Primary Examiner — Matthew Coughlin
(74) Attorney, Agent, or Firm — Michael Best & Friedrich LLP

(57) ABSTRACT

Disclosed herein are compounds and compositions useful for reducing the risk of infection. In particular, disclosed herein are mandelic acid condensation polymers, compositions comprising such compounds, processes for producing such compounds, and methods of using such compounds.

13 Claims, 7 Drawing Sheets

(56) References Cited

OTHER PUBLICATIONS

Herold, B.C., et al., "Bile salts: natural detergents for the prevention of sexually transmitted diseases." Antimicrob. Agents Chemother. 1999, 43, 745-751.
Roddy, R.E., et al., "Microbicides, meta-analysis, and the N-9 question." Sex Transm. Dis. 1998, 25, 151-153.
Roddy, R.E et al., "A controlled trial of nonoxynol-9 film to reduce male-to-female transmission of sexually transmitted diseases." N. Engl. J. Med. 1998, 339, 505-510.
Centers for Disease Control and Prevention. "CDC statement on study results of products containing nonoxynol-9." JAMA 2000, 284, p. 1376.
Stephenson, J., "Widely used spermicide may increase, not decrease, risk of HIV transmission." JAMA 2000, 284, 949.
Anderson, Robert A., et al., "Nitric Oxide-Dependent Human Acrosomal Loss Induced by PPCM (SAMMA) and by Nitric Oxide Donors Occurs by Independent Pathways: Basis for Synthesis of an Improved Contraceptive Microbicide," Journal of Andrology, vol. 30, No. 2, Mar./Apr. 2009, 168-182.
Anderson, Robert A., et al., "Feasibility of Repurposing the Polyanionic Microbicide, PPCM, for Prophylaxis against HIV Transmission during ART," Obstetrics and Gynecology vol. 2011; 1-13.
Mesquita et al., "Candidate Microbicide PPCM Blocks Human Immunodeficiency Virus Type 1 Infection in Cell and Tissue Cultures and Prevents Genital Herpes in a Murine Model," Journal of Virology, Jul. 2008, p. 6576-6584.
Whitesell et al., "Homochiral and Heterochiral Polyesters: Polymers Derived from Mandelic Acid," Chem. Mater. 1990, 2, pp. 248-254.
Lynch et al., "Structure of (S,S)-3,6-Diphenyl-1,4-dioxane-2,5-dioxane," Acta Cryst. (1990). C46, pp. 1125-1127.
European Patent Office Extended Search Report for Application No. 12854430.1 dated Aug. 27, 2015 (6 pages).

* cited by examiner

MANDELIC ACID CONDENSATION POLYMERS

CROSS-REFERENCE TO RELATED APPLICATIONS

This is a U.S. national stage entry of International Patent Application No. PCT/US2012/067452, filed on Nov. 30, 2012, which claims priority to U.S. Patent Application No. 61/566,441, filed on Dec. 2, 2011, the entire contents of all of which are fully incorporated herein by reference.

STATEMENT OF GOVERNMENT INTEREST

This invention was made with government support under contract nos. R43AI084225-01A2 and P01 HD41763-03, awarded by the National Institutes of Health. The government has certain rights in the invention.

TECHNICAL FIELD

The present disclosure relates generally to acid condensation polymers, and more particularly, to mandelic acid condensation polymers, compositions comprising such compounds, methods of using such compounds and compositions, and processes for preparing such compounds.

BACKGROUND

The HIV/AIDS epidemic has significantly and dramatically underscored the threat of STDs to the human population. Until there is a cure, or at least an effective treatment, the best, and perhaps only realistic, approach to this increasing problem of STDs (especially HIV/AIDS) appears to be reducing the risk of transmission of STDs by the causative pathogens and thus reducing the number of new infections. Even when STD treatments or cures become available, prevention will likely remain as the first line of defense for economic and medical reasons.

At present, education in regard to STDs, their modes of transmission, and so-called "safe-sex" techniques has, at least to some degree in the more developed countries, shown promise in reducing the risks of STD transmission through sexual activity. Screening of the blood supply has helped to reduce the risk of transmission of such STD-causing organisms via blood transfusions and related medical practices. Nonetheless, the spread of such STDs has not been halted to a satisfactory degree even in developed countries with active and progressive education programs. Even with their known effectiveness in preventing STDs, current safe-sex techniques are not always used, or are not always used properly, for many reasons (e.g., carelessness, lack of knowledge, improper techniques, cultural barriers, unplanned or spontaneous sexual activity, and the like). Moreover, even when used correctly, safe-sex techniques are not always effective. Various birth control devices—including barrier methods and vaginal contraceptives—are currently available. Some of these may, in addition, also have a least some degree of anti-STD activity.

Sexually transmitted diseases, especially HIV/AIDS, also present risks to health care providers and laboratory personnel working with STD-infected patients and/or blood and tissue samples from such patients. Physical contact with the bodily fluids of infected patients can, especially if there are breaks or cuts in the skin, increase the risk of transmission of the STD-causing organisms. In recent years, such health care providers and laboratory personnel have increasingly donned protective clothing and equipment when working with patients or biological samples where exposure to bodily fluids is possible. Latex gloves (often double or triple layered), goggles, protective clothing, and the like are often used when treating or examining patients in both medical and dental offices or working with biological samples from patients (e.g., blood, tissue, and the like). In spite of these precautions, exposure to bodily fluids can still occur. For example, sudden movement by a patient while having a blood sample withdrawn can cause blood to splatter and, perhaps, come in contact with an unprotected part of the body of other persons in the area; needle punctures or scalpel cuts can expose health-care providers to bodily fluids in spite of gloves and other protective layers; or aerosols containing blood and/or saliva can be generated during dental procedures which may contact the body of other persons. Although contact with unbroken and healthy skin is unlikely to result in transmission of the STD, breaks, cuts, or damage to the protective skin layer can increase the risk of transmission.

Treatments are available for many STDs subsequent to infection, but such infections are increasingly showing resistance to available treatments. For example, HIV can become drug resistant to convention antiretroviral therapies. This phenomenon is well established and is monitored by the WHO in developing countries. In the Unites States, 50% of HIV patients receiving treatment are known to be infected with a strain of HIV that expresses resistance to at least one known treatment drug. In one study, nearly 30% of new HIV infections in one region of Africa were of a drug-resistant strain. The particular drug had been introduced only 18 months earlier. Patients with HIV must be monitored for such drug resistance and are typically on a cocktail of drugs to maintain suppression of the infection. Not only can a sexually active person become infected with an already drug resistant strain, but once infected and under treatment, HIV can mutate and thus become resistant to further treatment.

Accordingly, what is needed are improved compounds, compositions, and methods for reducing the risk of STD infections. It would be desirable if such compounds, compositions, and methods would not interfere with the natural and protective vaginal mechanisms so as to maintain the naturally protective vaginal flora and maintain integrity of vaginal and cervical tissues, yet prevent pathogens from infecting host cells such as macrophages and CD4+ cells. It would also be desirable if such compounds, compositions, and methods would be relatively easy to use and have significantly fewer side effects than currently available products so that it would more likely be used on a consistent basis. It would also be desirable if such compounds, compositions, and methods could be used in heterosexual, homosexual, and bisexual relationships and for a wide range of sexual activities. It would also be desirable if such compounds, compositions, and methods could be implemented by either party to the sexual activity. It would also be desirable to provide compounds, compositions, and methods by which the risk of infection by sexually transmitted diseases, especially HIV/AIDS, could be reduced for individuals working with patients and/or biological samples.

SUMMARY

In one aspect, compounds having formula (I) are disclosed,

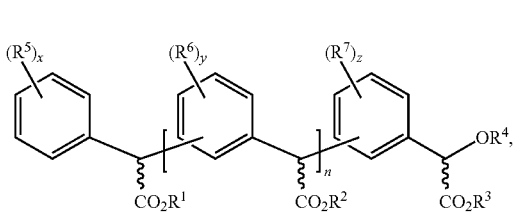

or a pharmaceutically acceptable salt, ester, amide, or prodrug form thereof,
wherein
$R^1$, $R^2$, and $R^3$ are each independently selected from the group consisting of hydrogen, alkyl, alkenyl, alkynyl, cycloalkyl, heterocycle, heteroaryl, aryl, and counterion;
$R^4$ is independently selected from the group consisting of hydrogen, alkyl, alkenyl, alkynyl, cycloalkyl, heterocycle, heteroaryl, and aryl;
$R^5$, $R^6$, and $R^7$ are each independently selected from the group consisting of alkyl, alkoxy, hydroxy, and halogen;
n is an integer greater than zero; and
x, y, and z are each an integer independently selected from the group consisting of 0, 1, 2, 3, and 4.

In another aspect, compounds having repeating units of formula (II) are disclosed,

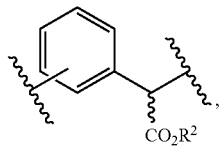

or a pharmaceutically acceptable salt, ester, amide, or prodrug form thereof,
wherein
$R^2$ is independently selected from the group consisting of hydrogen, alkyl, alkenyl, alkynyl, cycloalkyl, heterocycle, heteroaryl, aryl, and counterion.

In another aspect, disclosed are compositions comprising a compound of the invention and a pharmaceutically acceptable carrier. Preferably, the compositions are adapted for topical use as protective agents against transmission of one or more sexually transmitted diseases, and in particular, HIV/HSV.

In yet another aspect, disclosed is a process for producing a compound of the invention. In one embodiment, the process comprises cooling a strong acid to a temperature below 0° C., preferably below −10° C., more preferably below −25° C., and most preferably below about −30° C.; and adding mandelic acid or a mandelic acid derivative to the strong acid to provide a reaction mixture. In another embodiment, the process comprises providing a reaction mixture comprising mandelic acid or a mandelic acid derivative and a strong acid, wherein the reaction mixture is at a reduced temperature ranging from about −45° C. to about −5° C., preferably from about −35° C. to −30° C.

In another aspect, disclosed is a method for reducing the risk of infection. In one embodiment, the method comprises applying to the body or portion of the body of an individual an effective amount of a protective agent, wherein the protective agent comprises a compound of the invention. In another embodiment, the method comprises contacting a pathogen or cells susceptible to infection by the pathogen with an effective amount of a compound of the invention, thereby reducing the risk of transmission of the pathogen.

The compounds, compositions, methods and processes are further described herein.

DETAILED DESCRIPTION

Definition of Terms

Figure 1:
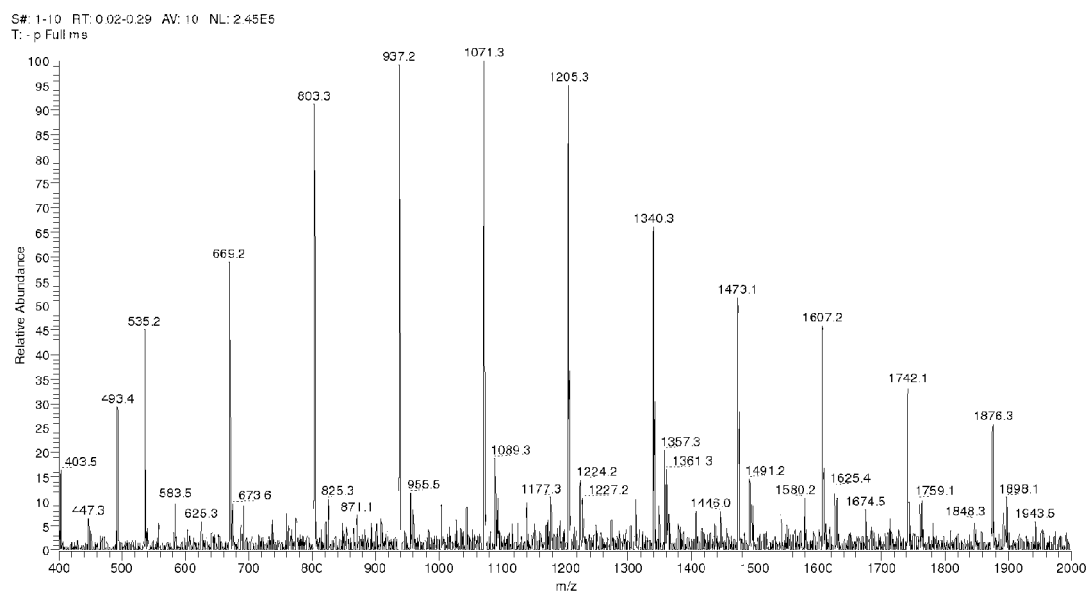
FIG. 1 shows an ESI-MS spectrum of an embodiment of the present invention.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "suitable substituent" is intended to mean a chemically and pharmaceutically acceptable functional group i.e., a moiety that does not negate the biological activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents.

As used herein, the term "alkyl" refers to a linear or branched hydrocarbon radical having 1, 2, 3, 4, 5, 6, 7, 8, 9, or 10 carbons. Alkyl groups of the present invention include, but are not limited to, methyl, ethyl, n-propyl, isopropyl, n-butyl, iso-butyl, secondary-butyl, and tertiary-butyl. Alkyl groups of the present invention may be unsubstituted or substituted by one or more suitable substituents, preferably 1 to 3 suitable substituents, as defined above. Preferred alkyls include ($C_1$-$C_6$) alkyl, more preferred are ($C_1$-$C_4$) alkyl, and most preferred are methyl and ethyl.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "halogen" refers to a fluoro, chloro, bromo or iodo radical.

As used herein, the term "alkenyl" refers to a straight or branched hydrocarbon radical having 2, 3, 4, 5, 6, 7, 8, 9 or 10 carbons, and having one or more carbon-carbon double bonds. Alkenyl groups of the present invention include, but are not limited to, ethenyl, 1-propenyl, 2-propenyl (allyl), iso-propenyl, 2-methyl-1-propenyl, 1-butenyl, and 2-butenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present invention include, but are not limited to, ethynyl, propynyl, and butynyl. Alkynyl groups of the present invention may be unsubstituted or substituted by one or more suitable substituents, preferably 1 to 3 suitable substituents, as defined above.

As used herein, the term "carbonyl" or "(C=O)" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "oxo" refers to a double bonded oxygen (=O) radical wherein the bond partner is a carbon atom. Such a radical can also be thought as a carbonyl group.

As used herein, the term "aryl" means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

As used herein, the term "heteroaryl" means a monocyclic, bicyclic, or tricyclic aromatic heterocyclic group containing one or more heteroatoms selected from O, S and N in the ring(s). Heteroaryl groups of the present invention include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups of the present invention may be unsubstituted or substituted by one or more suitable substituents, preferably 1 to 5 suitable substituents, as defined above.

As used herein, the term "heterocycle" refers to a monocyclic, bicyclic, or tricyclic group containing 1 to 4 heteroatoms selected from N, O, $S(O)_n$, NH or NR, wherein R is a suitable substituent. Heterocyclic groups of the present invention optionally contain 1 or 2 double bonds. Heterocyclic groups of the present invention include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups of the present invention may be unsubstituted or substituted by one or more suitable substituents, preferably 1 to 3 suitable substituents, as defined above.

As used herein, the term "hydroxy" refers to an —OH group.

As used herein, the term "counterion" refers to a cationic species that is a suitable counterion for a carboxylate group. Suitable counterions of the present invention include, but are not limited to, sodium cation, potassium cation, calcium cation, magnesium cation, and ammonium cation.

Compounds

Disclosed herein are mandelic acid condensation polymers, also referred to herein as polyphenylenecarboxymethylene (PPCM) compounds. The inventors have unexpectedly and surprisingly discovered that these compounds can be obtained by acid catalyzed polymerization of mandelic acid under controlled reaction conditions. In particular, it has been discovered that reaction temperature, rate of addition of reactants, and reaction medium are important factors in obtaining mandelic acid condensation polymers of the present invention. By conducting the acid-catalyzed polymerization of mandelic acid or a mandelic acid derivative at reduced temperature, specifically below 0° C., preferably below −10° C., more preferably below −25° C., and most preferably below about −30° C.; by controlling the rate of addition of mandelic acid reactant to the reaction mixture; and by use of neat reaction conditions, mandelic acid condensation polymers of the present invention can be selectively formed and obtained in high yield.

In one aspect, mandelic acid condensation polymers of the present invention have formula (I),

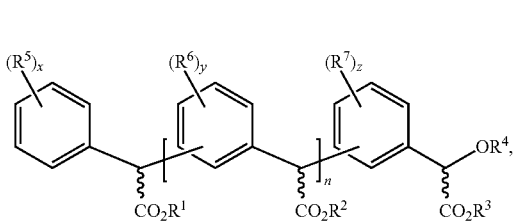

(I)

or a pharmaceutically acceptable salt, ester, amide, or prodrug form thereof, wherein $R^1$, $R^2$, and $R^3$ are each independently selected from the group consisting of hydrogen, alkyl, alkenyl, alkynyl, cycloalkyl, heterocycle, heteroaryl, aryl, and counterion;

$R^4$ is independently selected from the group consisting of hydrogen, alkyl, alkenyl, alkynyl, cycloalkyl, heterocycle, heteroaryl, and aryl;

$R^5$, $R^6$, and $R^7$ are each independently selected from the group consisting of alkyl, alkoxy, hydroxy, and halogen;

n is an integer greater than zero; and x, y, and z are each an integer independently selected from the group consisting of 0, 1, 2, 3, and 4.

In certain embodiments, n is an integer selected from 1 to 70, more preferably an integer selected from 1 to 60, and most preferably an integer selected from 10 to 22.

In a preferred embodiment, $R^1$, $R^2$, $R^3$, and $R^4$ are each hydrogen; and x, y, and z are each zero. Preferably, n is an integer selected from 1 to 70, more preferably an integer selected from 1 to 60, and most preferably an integer selected from 10 to 22.

In another preferred embodiment, $R^1$, $R^2$, $R^3$, are each methyl; $R^4$ is hydrogen; and x, y, and z are each zero. Preferably, n is an integer selected from 1 to 70, more preferably an integer selected from 1 to 60, and most preferably an integer selected from 10 to 22.

In another preferred embodiment, $R^1$, $R^2$, and $R^3$ are each sodium cation; $R^4$ is hydrogen; and x, y, and z are each zero. Preferably, n is an integer selected from 1 to 70, more preferably an integer selected from 1 to 60, and most preferably an integer selected from 10 to 22.

In certain embodiments, the compounds of the invention can have the structural formula (I-A),

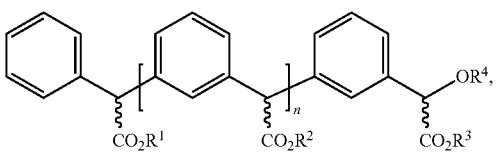

(I-A)

wherein $R^1$, $R^2$, $R^3$, $R^4$, and n are as previously defined.

In certain embodiments, the compounds of the invention can have the structural formula (I-B),

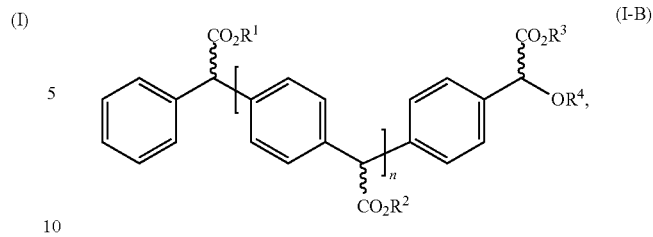

(I-B)

wherein $R^1$, $R^2$, $R^3$, $R^4$, and n are as previously defined.

In another aspect, polyphenylenecarboxymethylene compounds according to the present invention are compounds having repeating units of formula (II),

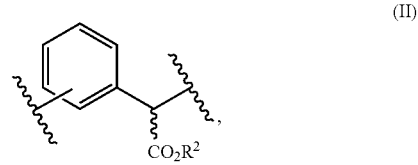

(II)

or a pharmaceutically acceptable salt, ester, amide, or prodrug form thereof, wherein $R^2$ in each repeating unit is independently selected from the group consisting of hydrogen, alkyl, alkenyl, alkynyl, cycloalkyl, heterocycle, heteroaryl, aryl, and counterion.

Preferably, the polyphenylenecarboxymethylene compounds have about 1 to about 60 repeating units, preferably about 1 to about 20 repeating units, and most preferably about 10 to about 22 repeating units.

In a preferred embodiment, the polyphenylenecarboxymethylene compounds comprise repeating units of formula (II) wherein $R^2$ is selected from hydrogen. In another preferred embodiment, the polyphenylenecarboxymethylene compounds comprise repeating units of formula (II) wherein $R^2$ is selected from methyl. In another preferred embodiment, the polyphenylenecarboxymethylene compounds comprise repeating units of formula (II) wherein $R^2$ is selected from sodium cation. In certain embodiments, the polyphenylenecarboxymethylene compounds comprise repeating units of formula (II) wherein $R^2$ is variable, preferably independently selected from hydrogen, methyl, and sodium cation.

The compounds of the invention contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

Specific embodiments of the present invention include compounds disclosed in the Examples provided herein, and the pharmaceutically acceptable salt, ester, amide, and prodrug forms thereof.

Bulk Polymer Compositions

The compounds of the invention can be prepared and isolated as polymeric compositions comprising a distribution of compounds of formula (I). Preferably, the composition comprises a distribution of compounds of formula (I) wherein n ranges from 1 to 70, more preferably from 1 to 60, and most preferably from 10 to 22, and specifically preferably wherein n averages about 20.

In a preferred embodiment, the polymeric compositions comprise compounds of formula (I) wherein $R^1$, $R^2$, $R^3$, and $R^4$ are each hydrogen; and x, y, and z are each zero. In another preferred embodiment, the polymeric compositions comprise compounds of formula (I) wherein $R^1$, $R^2$, $R^3$, are each methyl; $R^4$ is hydrogen; and x, y, and z are each zero. In another preferred embodiment, the polymeric compositions comprise compounds of formula (I) wherein $R^1$, $R^2$, and $R^3$ are each sodium cation; $R^4$ is hydrogen; and x, y, and z are each zero. In certain embodiments, the polymeric compositions comprise a distribution of compounds of formula (I) wherein $R^1$, $R^2$, $R^3$, and $R^4$ are variable among compounds of the composition, and optionally within the individual compounds of the composition.

The compounds of the invention can be prepared and isolated as polymeric compositions comprising a distribution of polyphenylenecarboxymethylene compounds having repeating units of formula (II). Preferably, the composition comprises a distribution of polyphenylenecarboxymethylene compounds having about 1 to about 60 repeating units of formula (II), preferably about 1 to about 20 repeating units of formula (II), and most preferably about 10 to about 22 repeating units of formula (II).

In a preferred embodiment, the polymeric compositions comprise polyphenylenecarboxymethylene compounds having repeating units of formula (II) wherein $R^2$ is selected from hydrogen. In another preferred embodiment, the polymeric compositions comprise polyphenylenecarboxymethylene compounds having repeating units of formula (II) wherein $R^2$ is selected from methyl. In another preferred embodiment, the polymeric compositions comprise polyphenylenecarboxymethylene compounds having repeating units of formula (II) wherein $R^2$ is selected from sodium cation. In certain embodiments, the polymeric compositions comprise polyphenylenecarboxymethylene compounds having repeating units of formula (II) wherein $R^2$ is variable among compounds of the composition, and optionally within individual compounds of the composition, preferably where $R^2$ is independently selected from hydrogen, methyl, and sodium cation.

In general, the bulk polymer compositions of the present invention have a molecular weight range from about 200 to about 10,000 daltons (Da), preferably from about 400 to about 8,000 Da, most preferably from about 600 to about 6,000 Da, and specifically preferably from about 2,000 to about 6,500 Da.

Synthetic Methods

The compounds and compositions of the invention can be better understood in connection with the following synthetic schemes and methods which illustrate a means by which the polymers can be prepared.

Scheme 1

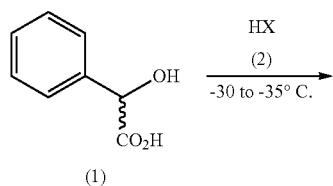

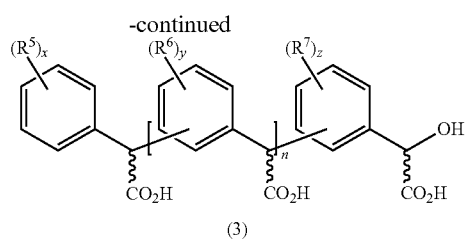

(3)

Mandelic acid condensation polymers of formula (3) can be prepared as described in Scheme 1. Treatment of dl-mandelic acid (1), a mandelic acid derivative, or a combination thereof, with a strong acid (2), preferably concentrated sulfuric acid, will provide mandelic acid condensation polymers of formula (3). Preferably, the polymerization reaction is conducted at a temperature below 0° C., preferably from about −45° C. to about −5° C., more preferably from about −40° C. to about −15° C., most preferably from about −35° C. to about −30° C.

In certain embodiments, the polymerization reaction is conducted in the absence of solvent, and thus under neat reaction conditions. For example, the strong acid of formula (2), preferably concentrated sulfuric acid, may serve as both the acid catalyst for polymerization and the reaction medium.

In certain embodiments, the polymerization reaction is conducted by first cooling the strong acid to a temperature below 0° C., preferably from about −45° C. to about −5° C., more preferably from about −40° C. to about −15° C., most preferably from about −35° C. to about −30° C.; followed by addition of the mandelic acid reactant. Where the polymerization is conducted on a large scale, preferably the mandelic acid is added in aliquots over an extended time period (e.g., 30 minutes).

Scheme 2

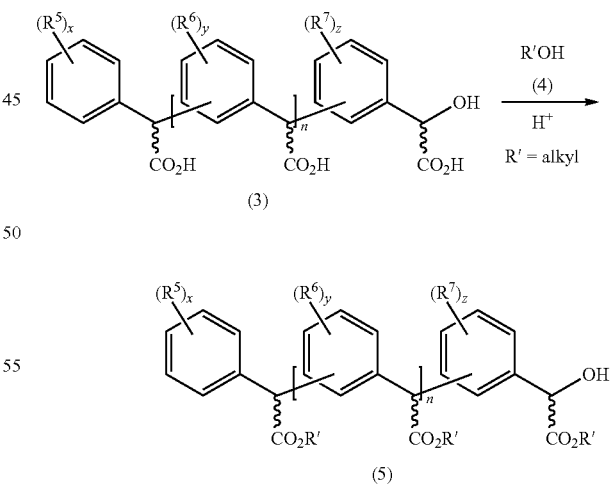

Ester derivatives of the mandelic acid condensation polymers of the present invention can be prepared as described in Scheme 2. Mandelic acid condensation polymers of formula (3), when treated with an alcohol of formula (4), such as methanol, in the presence of an acid catalyst, such as sulfuric acid, will provide ester derivatives of formula (5).

Scheme 3

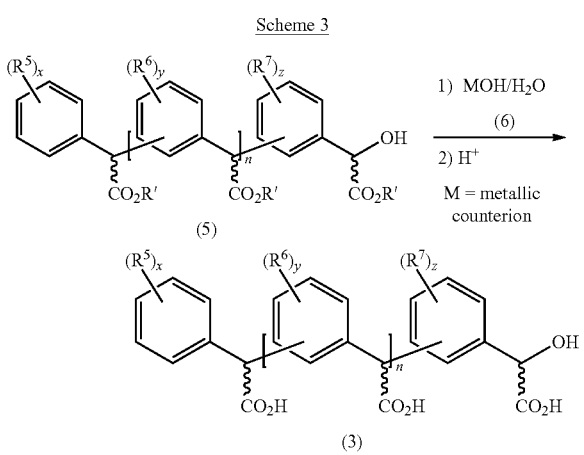

The ester derivatives of formula (5) can be hydrolyzed to the free acid as described in Scheme 3. Ester derivatives of formula (5), when treated with a strong base (MOH) of formula (6) (e.g., sodium hydroxide) in aqueous solvent, followed by acid quench (e.g., with hydrochloric acid) will provide mandelic acid condensation polymers of formula (3).

Scheme 4

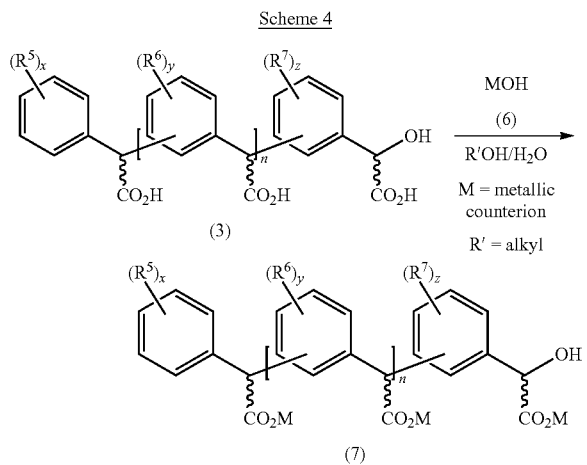

Salts of the mandelic acid condensation polymers of the present invention can be prepared as described in Scheme 4. Mandelic acid condensation polymers of formula (3), when treated with a strong base of formula (6) (e.g., sodium hydroxide) in an alcoholic/aqueous solvent, will provide salt derivatives of formula (7), such as the sodium salt form (i.e., M=Na).

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

Compositions for Reducing the Risk of Infection

The compounds of the invention, including bulk polymeric compositions comprising a distribution of polymeric compounds of the invention, can be formulated into compositions useful for reducing the risk of transmission of viral and bacterial infections. A compound or composition of the invention can be adapted for topical administration to a subject, including dermal, intravaginal or intrarectal use, including a suppository, a bioadhesive polymer, or a vaginal disk, which can provide timed release of protective agent. Optionally, compounds and compositions of the present invention can be formulated in combination with a solid substrate to produce a condom, diaphragm, sponge, tampon, a glove or the like, which can be composed, for example, of an organic polymer such as polyvinyl chloride, latex, polyurethane, polyacrylate, polyester, polyethylene terephthalate, poly(ethylene-co-vinyl acetate); polymethacrylate, silicone rubber, a silicon elastomer, polystyrene, polycarbonate, a polysulfone, or the like.

For topical administration, compounds and compositions of the present invention can be formulated into a composition with any pharmaceutically acceptable carrier. Topical compositions of the present invention can be, for example, in the form of a cream, a foam, a jelly, a lotion, an ointment, a solution, a spray, or a gel. In addition, compositions according to the invention can contain one or more additional agents, for example, an antimicrobial agent such as an antibiotic or an antimicrobial dye such as methylene blue or gentian violet; an antiviral agent such as a nucleoside analog, a zinc salt, or a cellulose phthalate such as cellulose acetate phthalate or a hydroxypropyl methylcellulose phthalate; a contraceptive; a lubricant, or any agent generally useful to a sexually active individual.

A pharmaceutically acceptable carrier useful in a composition of the invention can be aqueous or non-aqueous, for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the compounds of the invention, for example, carbohydrates, such as glucose, sucrose or dextrans, antioxidants, such as ascorbic acid or glutathione, chelating agents, low molecular weight proteins or other stabilizers or excipients.

The pharmaceutical compositions also can comprise an admixture with an organic or inorganic carrier or excipient suitable for intravaginal or intrarectal administration, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening or coloring agents and perfumes can be used, for example a stabilizing dry agent such as triulose.

Compounds and bulk polymeric compositions of the invention can be incorporated within an encapsulating material such as into an oil-in-water emulsion, a microemulsion, micelle, mixed micelle, liposome, microsphere or other polymer matrix. Liposomes, for example, which consist of phospholipids or other lipids, are nontoxic, physiologically acceptable and metabolizable carriers that are relatively simple to make and administer.

Compositions of the present invention may be used at or about the time of sexual activity, and more preferably prior to initiating sexual contact. The manner of use will depend, in part, on the form of the composition, for example, whether the composition is in a liquid or liquid-like form such as a jelly, a douche, a cream or the like, or whether the compounds of the invention are formulated with a solid substrate such as a sponge, diaphragm, tampon, pessary, condom or the like. When formulated as such a composition, compounds of the present invention can be impregnated into an absorptive material such as a sponge or tampon, or coated onto the surface of a relatively impermeable solid substrate such as a condom or diaphragm, or on medical gloves.

The amount of the compounds of the present invention in a composition can be varied, depending on the type of composition, such that the amount present is sufficient to reduce the ability of a pathogen to attach and enter a host cell. An effective amount of a compound of the present invention can block infection of susceptible cells by a pathogen such as free HIV, or cell-associated HIV present in a secretion, or by uptake of the pathogen due to binding to otherwise non-susceptible cells, which then transfer the pathogen to susceptible cells. An example of such an amount is about 1 to 100 mM, generally about 5 to 30 mM, when administered in an ointment, gel, foam, spray or the like, or about 0.1 to 2 grams, generally about 0.25 to 0.75 grams, when administered as a suppository or in combination with a solid substrate. An effective amount of a compound of the present invention also can be measured in a weight:weight (w:w) or weight:volume (w:v) amount, for example, about 0.1% to 4% w:w with respect to a solid substrate or about 0.1% to 4% w:v with respect to a pharmaceutically acceptable carrier. In addition, an amount of a compound of the present invention sufficient to reducing the risk of transmission of a sexually transmitted disease can be determined using routine clinical methods.

Methods

The compounds and compositions of the present invention are useful for reducing the risk of infection by blocking pathogenic attachment and entry into host cells. In particular, the compounds and compositions are useful as noncytotoxic, broad-spectrum, antimicrobial agents with anti-HIV, anti-HSV, and anti-bacterial activities. The compounds and compositions are compatible with natural and protective vaginal mechanisms; are relatively easy to use; and have significantly fewer side effects than currently available products. The compounds and compositions can be used in heterosexual, homosexual, and bisexual relationships and for a wide range of sexual activities. The compounds and compositions are useful for reducing the risk of infection by sexually transmitted diseases, especially HIV/AIDS, for individuals working with patients and/or biological samples.

A method for protecting an individual from contracting a disease through contact with a bodily fluid comprises applying to the body or portion of the body of the individual an effective amount of a compound or composition of the present invention, also referred to herein as a protective agent. A method of reducing the risk of transmission of a sexually transmitted pathogen to a human subject comprises contacting the pathogen or cells susceptible to infection by the pathogen with an effective amount of a compound or composition of the present invention, thereby reducing the risk of transmission of the pathogen. In one preferred embodiment, an effective amount of a compound or composition of the present invention is administered topically to the subject in need thereof before or after sexual intercourse. In another preferred embodiment, an effective amount of a compound or composition of the present invention is added to bodily fluids, such as semen, for the purpose of removing or inhibiting pathogens.

The compounds and compositions can be used to inhibit proliferation of microbial cells, such as those associated with a sexually transmitted disease or infection. Contacting the microbial cell with one or more of the compounds of the present invention interferes with, inhibits or prevents a function or activity of the cell necessary for cellular proliferation. Cell proliferation assays, as are known and standard in the art, can be used to determine the efficacy of the compounds and compositions as an anti-proliferative agents.

It is contemplated that the topical compounds and compositions of the present invention are effective against drug-resistant sexually transmitted diseases as well as emerging infectious diseases transmitted via body fluids, particularly semen, vaginal fluid, saliva, and rectal or anal mucus. The sexually transmitted diseases or infections that the compounds and compositions are effective against include, but are not limited to, HIV/AIDS, HPV (also called genital warts), HSV, chancroid (*Haemophilus ducreyi*), chlamydia (*Chlamydia trachomatis*), crab lice, gonorrhea (*Neisseria gonorrhoeae*), hepatitis, lymphogranuloma venereum (LGV, *Chlamydia trachomatis*), molluscum contagiosum (poxvirus of the Molluscipox virus genus), nongonococcal urethritis (NGU), pelvic inflammatory disease (PID), scabies (the skin mite *Sarcoptes scabiei*), syphilis (*Treponema pallidum*), and vaginitis (trichomoniasis).

The individual of the methods disclosed herein includes any individual that is at risk of transmission of a sexually transmitted disease, including sexually active individuals and individuals that may be exposed to sexually transmitted diseases through other means. The subject may be female. In such cases, the compounds and compositions can be administered as a vaginal or rectal ointment, which is applied buccally, vaginally and/or rectally, such as, for example, as a suppository. An average vaginal dose may be delivered in a 2% ointment with about 18 mg/mL of protective agent, delivering about 90 mg per 5 mL or a 1% ointment with about 9 mg/mL of protective agent delivering about 45 mg per 5 mL.

Alternatively, the subject is male. In such cases, the compounds and compositions may be administered via the rectum as a topical ointment applied buccally and/or rectally, such as, for example, as a suppository, or to the penis as a cream, ointment, spray, or lubricant for use with or without a condom. Alternatively, the subject at risk has been diagnosed with a sexually transmitted disease or infection.

Methods of the present invention also encompass co-administering to a patient in need of the protective agents of the present invention another drug effective against a sexually transmitted disease or infection (anti-STD drug). For example, and without being limiting, a person with HIV may have a compound or composition of the present invention co-administered with highly active antiretroviral therapies (HAART). These include, for example, Nucleoside Reverse Transcription Inhibitor (NRTIs) such as Zidovudine, Didanosine, Zalcitabine, Stavudine, Lamivudine, Abacavir, Tenofovir; Nonnucleoside Reverse Transcriptase Inhibitors (NNRTIs) such as Nevirapine, Delavirdine, Efavirenz; Protease Inhibitors such as Indinavir, Ritonavir, Nelfinavir, Saquinavir, Amprenavir, Lopinavir. One of ordinary skill in the art is well able to determine which drug therapy, including dose and dosing schedule, is suitable in combination with the protective agents disclosed herein based on a subject's medical history and the progression of the disease.

The compounds, compositions, methods and processes of the invention will be better understood by reference to the following examples, which are intended as an illustration of and not a limitation upon the scope of the invention.

EXAMPLES

Melting points reported herein were determined with a Thomas-Hoover capillary melting point apparatus and are uncorrected. $^1$H nuclear magnetic resonance (NMR) and $^{13}$C NMR spectra were determined using Bruker 300, 500 and 900 MHz FT NMR spectrometers. The chemical shifts (δ) are expressed in parts per million (ppm) relative to tetramethylsilane (TMS) as the internal standard. Splitting patterns are as follows: s, single; d, doublet; br, broad; m, multiplet. All mass spectra were recorded with Applied Biosystems Voyager DE PRO MALDI-TOF spectrometer and Finnigan LCQ for APCI and routine ESI-MS. Reversed phase high-performance liquid chromatography (HPLC) analyses were performed on a Nova-Pak® $C_{18}$ 60 Å 4 μm 3.9×300 mm column using a gradient of 50% $CH_3CN/H_2O$ (1 minute), 50% to 90% $CH_3CN$ (70 minutes), and 90% to 50% $CH_3CN$ (20 minutes) with a flow of 1 ml per minute and with detection at 254 nanometers (nm). The preparative HPLC were performed on a Nova-Pak® $C_{18}$ 6 μm 19×300 mm column using a gradient of 65% $CH_3CN/H_2O$ (1 minute), 65% to 90% $CH_3CN$ (90 minutes), and 90% to 65% $CH_3CN$ (30 minutes) with a flow of 3 ml per minute and with detection at 254 nm. For column chromatography, Fischer silica gel (100-200 mesh) was used. All solvents used were either HPLC grade (Fisher Scientific) or analytical grade (Aldrich). dl-Mandelic acid was purchased from Aldrich. All other chemicals were purchased from either Aldrich or Fisher Scientific.

Example 1

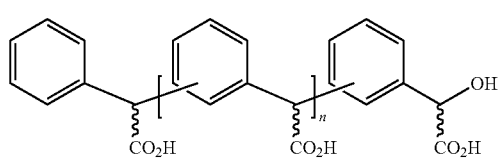
(3a)

A mandelic acid condensation polymer of formula (3a) was prepared by direct reaction of dl-mandelic acid with concentrated sulfuric acid at low temperature. dl-Mandelic acid (30.4 g, 200 mmol) was added in one lot to a round bottom flask equipped with a mechanical stirrer containing conc. $H_2SO_4$ (256 g, 4000 mmol, 139 ml) under vigorous stirring at −35° C. The resulting reaction mixture was stirred at −35° C. for 1 hour and then stirred at ambient temperature for an additional 8 hours. Subsequently, this reaction mixture was poured into a conical flask containing 3040 ml of ice water and stirred for 1 hour. The solid separated out and was filtered through suction, washed with water (3×50 ml) and dried under reduced pressure in vacuum desiccators for 12 hours to give (3a) as an off white solid (28.25 g, 100% yield); mp 205-206° C. $^1$H NMR (DMSO-d$_6$): δ 7.35-7.02 (m, ArH), 5.23 (br s, CHOH), 5.15-4.75 (m, CHCO$_2$H), 3.41 (br s, OH). $^{13}$C NMR (DMSO-d$_6$): δ 174.09, 140.23, 139.72, 138.85, 138.25, 129.38, 127.96, 56.76.

Example 2

ESI-MS Analysis

The structure of formula (3a) was further confirmed by electrospray ionization (ESI) mass spectrometry (MS). Several samples prepared according to the procedure of Example 1 were evaluated. As shown in FIG. 1, the ESI spectrum indicates that the product from Example 1 is a composition of polymers with repeating units of 134 atomic mass units (amu), which corresponds to the molecular weight of mandelic acid minus water.

Example 3

A second synthesis of the polymer of formula (3a) was achieved conducting the polymerization at −30° C. (±5 Degrees). Concentrated sulfuric acid was cooled to −30° C. The temperature was maintained at −30° C. (±5 Degrees) as mandelic acid was added as aliquots, over a period of time (approximately 30 minutes used for 20 gram reaction), to the cooled and stirred mixture. (Ratio of mandelic acid/concentrated sulfuric acid was 20 grams/100 ml). The reaction mixture was then stirred and maintained at −30° C. for one hour followed by allowing the temperature to slowly rise to room temperature and stirred for an additional 12 hours. The reaction mixture was then poured over/into an ice and DI water mixture (500 grams/200 ml). A light pink precipitate formed and was subsequently vacuum filtered, washed with water and then resuspended in 200 ml of DI water. The precipitate was collected by vacuum filtration and washed by repeated suspension in DI water (200 ml) followed by vacuum filtration until the final pH of the wash water was between 4 and 5. The final bulk solid was air dried overnight. The yield of the reaction provided approximately 18 grams of polymer product of formula (3a) for every 20 grams of mandelic acid starting material.

Example 4

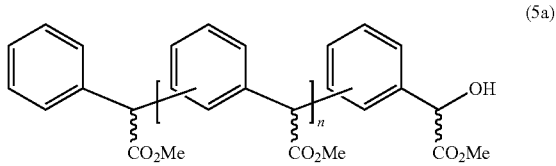
(5a)

An ester derivative of formula (5a) was prepared from the polymer of formula (3a). To a clear solution of the polymer formula (3a) (5.36 g, 40 mmol) in methanol (200 ml) was added 1.0 ml of conc. sulfuric acid and the resulting reaction mixture was heated at reflux temperature under stirring while removing water using a Dean-Stark trap for 8 hours. Solvent was removed under reduced pressure and dichloromethane (200 ml) was added to the residue. The reaction mixture was washed with 10% NaHCO$_3$ solution (3×30 ml). The aqueous phase was re-extracted with dichloromethane (2×50 ml). The combined organic phase was washed with brine (2×25 ml), dried over Na$_2$SO$_4$, filtered and concentrated in a rotary evaporator to give the polymer of formula (5a) as a white solid (5.78 g, 97.6% yield); mp 125-126° C. $^1$H NMR (CDCl$_3$): δ 7.26-6.96 (m, ArH), 5.30 (s, CHOH), 5.05-4.80 (m, CHCO$_2$CH$_3$), 3.76-3.46 (m, OCH$_3$).

Example 5

HPLC & LCQ-APCI Analysis

Figure 2:
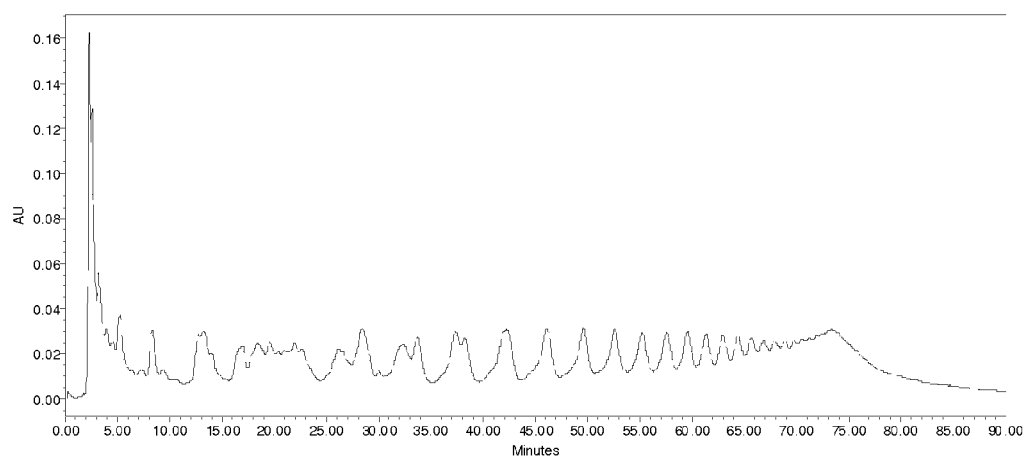
FIG. 2 shows an HPLC chromatogram of an embodiment of the present invention.

The structure of formula (5a), and thus that of formula (3a), was further confirmed by reverse phase HPLC and LCQ-APCI analyses. Reverse phase high performance liquid chromatography (HPLC) analysis of the product according to Example 4 using a Nova-Pak® C$_{18}$ 60 Å 4 μm 3.9×300 mm column provided the HPLC chromatogram shown in FIG. 2.

Figure 3:
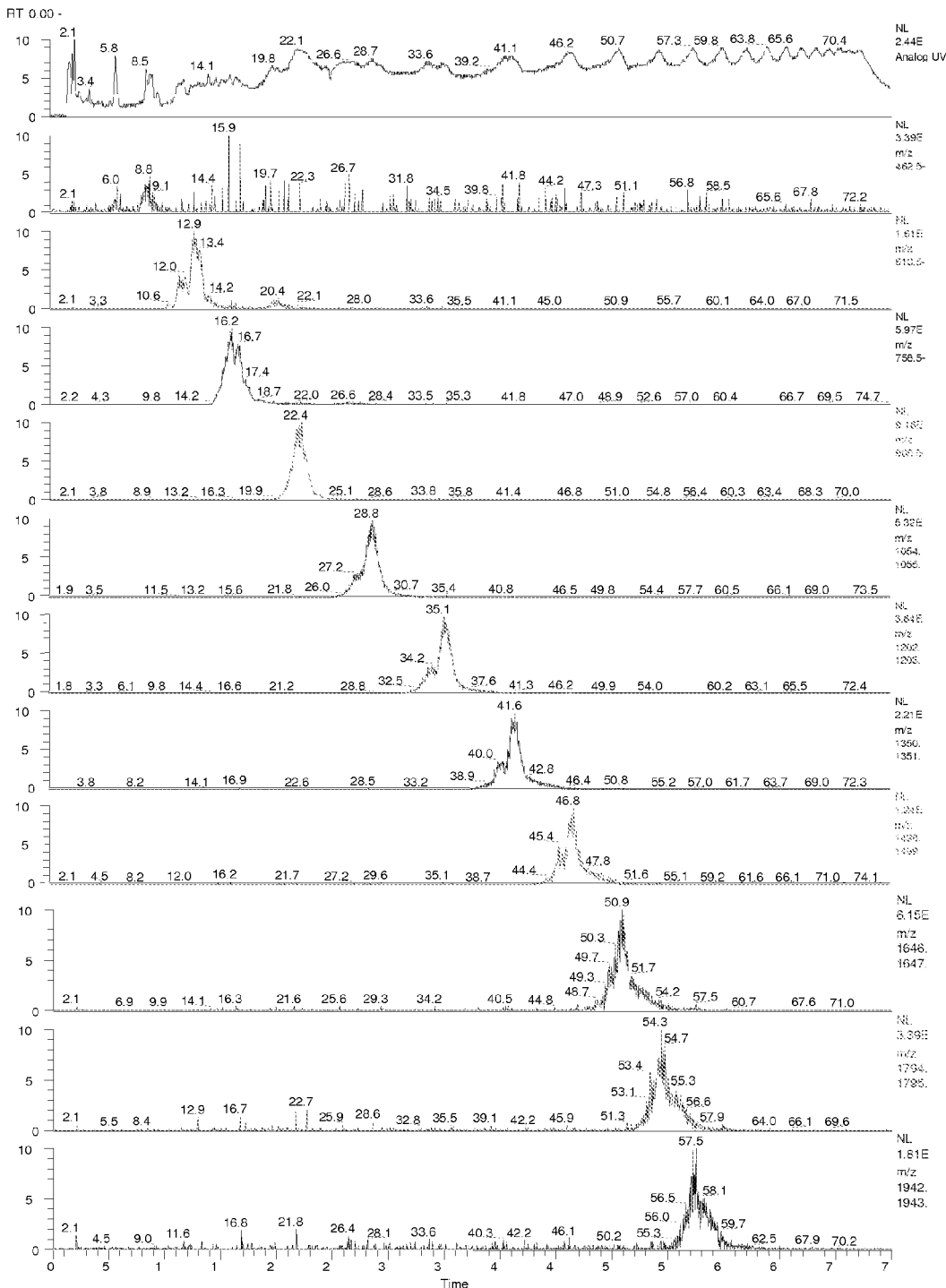
FIG. 3 shows an LCQ-APCI spectrum of an embodiment of the present invention.
Figure 4:
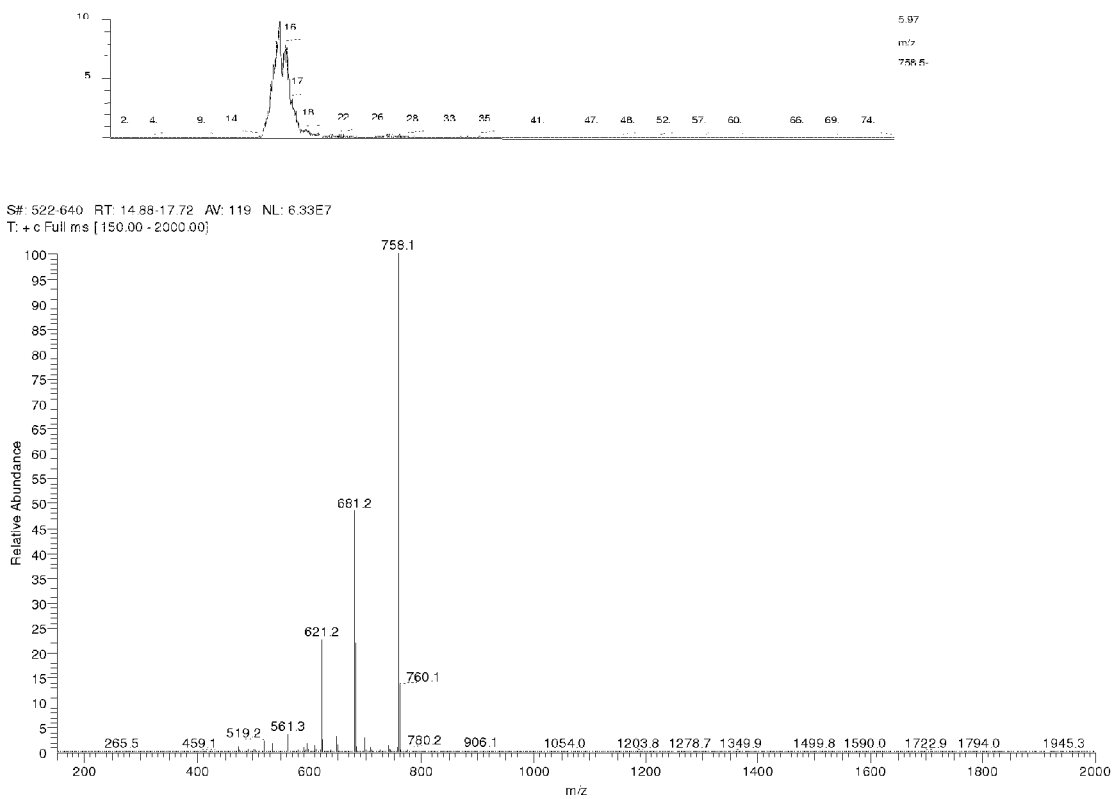
FIG. 4 shows an APCI-MS spectrum of an embodiment of the present invention.
Figure 5:
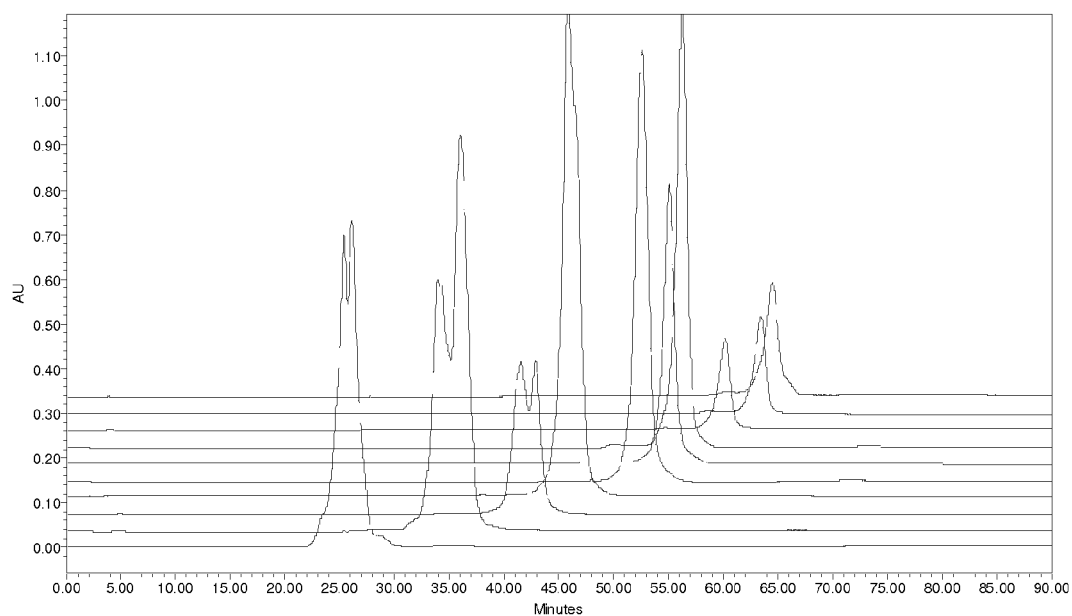
FIG. 5 shows an overlay of HPLC chromatograms of embodiments of the present invention.

To confirm the structure of the different peaks obtained from the reverse phase HPLC, the product according to Example 4 was analyzed with liquid chromatography quadrupole-atmospheric pressure chemical ionization (LCQ-APCI). FIG. 3 shows that the individual peaks each represent a polymer with repeating units of 148 atomic mass units. In particular, the parent molecular ion for each fraction from top to bottom in FIG. 3 has a mass to charge ratio (m/z) of 462.5, 610.5, 758.5, 905.5, 1054-1055, 1202-1203, 1350-1351, 1498-1499, 1646-1647, 1794-1795, and 1942-1943, respectively. These peaks correspond to, respectively, compounds of formula (5a) wherein n=1, 2, 3, 4, 5, 6, 7, 8, 9, 10, and 11. FIG. 4 shows the APCI-MS of the pure compound of formula (5a) wherein n=3. The individual polymers of the product according to Example 4 were separated via preparative phase HPLC using a Nova-Pak® C$_{18}$ 6 μm 19×300 mm column, as shown by the overlay of HPLC chromatograms in FIG. 5.

Example 6

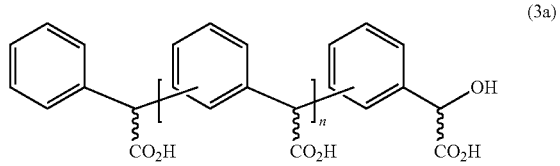
(3a)

The ester derivative of formula (5a) was successfully hydrolyzed back to the polymer of formula (3a). To a stirred suspension of the polymer of formula (5a) (444 mg, 3 mmol) in water (10 ml), a solution of NaOH (144 mg, 3.6 mmol) in water (10 ml) was added and the resulting reaction mixture was stirred at ambient temperature for 2 hours. By this time the compound was dissolved in water and a clear solution was obtained. To this solution conc. HCl (1.0 ml) was added and stirred for 30 min. Solid separated out and was filtered through suction, washed with water and dried under reduced pressure in a vacuum desiccator over CaCl$_2$ to give the polymer of formula (3a) as an off white solid (350 mg, 87.1% yield); mp 203-204° C. The resulting product was subjected to ESI-MS analysis, confirming a polymeric composition of compounds with repeating units of 134 atomic mass units.

Example 7

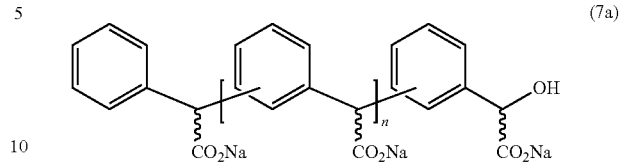
(7a)

A sodium salt form of the polymer of formula (3a) was prepared having the formula (7a). A clear solution of NaOH (9.24 g, 231 mmol) in water (10 ml) and ethanol (225 ml) was added to a solution of the polymer of formula (3a) (28.14 g, 210 mmol) in ethanol (350 ml) drop-wise under stirring at ambient temperature. The resulting reaction mixture was stirred at the same temperature for 1 hour. The solid separated out and was filtered through suction, washed with ethanol (2×40 ml) and dried under reduced pressure in vacuum desiccators over P$_2$O$_5$ & CaCl$_2$ to give the polymer of formula (7a) as an off white solid (30.40 g, 92.2% yield); mp 320-321° C. (d).

Example 8

A second synthesis of the sodium salt of formula (7a) was achieved. The free acid form of formula (3a) was dissolved in absolute ethanol (approx. 20 grams in 300 ml) and filtered. A saturated solution of sodium hydroxide in water/absolute ethanol was then added drop wise with vigorous stirring until the pH was 10-11. The fine powder precipitate was vacuum filtered quickly and repeatedly washed with absolute ethanol until the pH of the wash was neutral. The solid collected was immediately transferred into a vacuum desiccator for drying over night (24 hours under vacuum over H$_2$SO$_4$) resulting in a very fine white powder. The overall yield was approximately 20.5 grams of the salt of formula (7a) from about 18 grams of starting polymer of formula (3a).

Example 9

Acid Equivalent Titration

The structure of formula (7a), and thus that of formula (3a), was further confirmed by acid equivalent titration. An approximately 0.1 N solution of hydrochloric acid (HCl) was prepared by a known method and actual HCl concentration was determined by titrating a sample of sodium carbonate dissolved in water using thymol blue indicator; the concentration of HCl determined to be 0.103 N. The volume of titrant used was measured with a calibrated 10.0 milliliter (ml) buret. The sodium salt according to formula (7a) was dissolved in 10 ml of water and the solution was titrated with the 0.103 N HCl until a pink color persisted. Approximately 0.94±0.01 ml of 0.103 N HCl was required to achieve the end point for three samples, which indicated that there was one free carboxylate per 134 units of mass. These results are consistent with the structure of formula (7a). Furthermore, these results eliminate the possibility that the product is a polyester compound resulting from acid-catalyzed polyester formation from reaction of mandelic acid hydroxy functional groups with mandelic acid carboxylic acid functional groups.

Example 10

Ultra-High Field NMR Analysis

Figure 6:
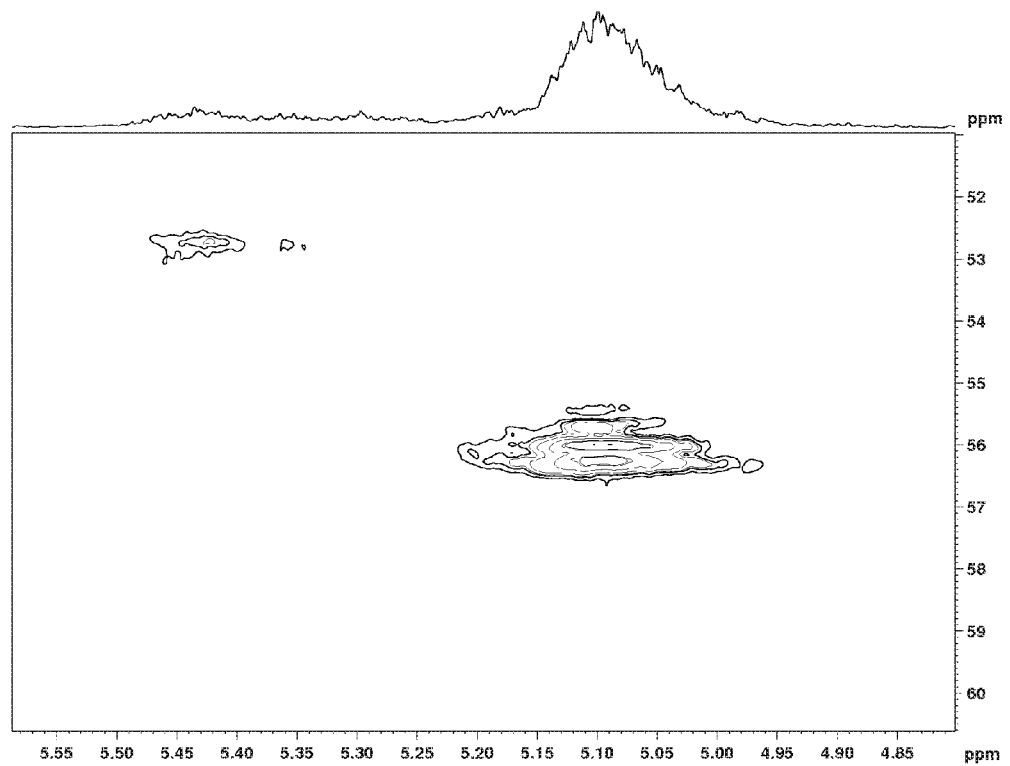
FIG. 6 shows an ultra-high field NMR analysis of an embodiment of the present invention.

To confirm the structure and stereochemical complexity of the compounds of the invention the different peaks obtained from the reverse phase HPLC, according to Example 5, were analyzed with ultra-high field FT NMR analysis. FIG. 6 shows the portion of a gradient selected heteronuclear single quantum correlation experiment (gsHSQC) of the compound of formula (5a), where n=4. Individual peaks each represent a correlation between a proton and carbon at particular chemical shift. Peak 1 (5.10-56.00 ppm) represents H—C—OH correlation, while peak 2 (5.43-52.72 ppm) represents H—C—$CO_2CH_3$. Resolving power of the 900 MHz spectrometer in both dimensions, as well as its sensitivity, allowed for unequivocal assignment of CHOH peak (peak 1) in the presence of other signals in the proton spectrum (shown as projection at the top of the spectrum in FIG. 6). Resolution in the horizontal (carbon) dimension indicates splitting pattern of the peak 2 in approximately 1:2:1 ratio, characteristic of all stereoisomeric forms.

Example 11

MALDI-TOF Analysis

Figure 7:
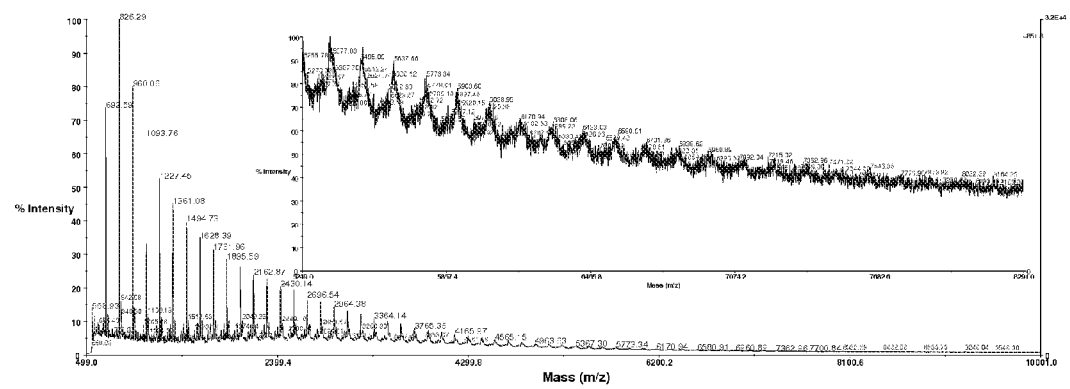
FIG. 7 shows a MALDI-TOF mass spectrum of an embodiment of the present invention.

The structure of formula (3a) was further confirmed and the polymer chain distribution in the bulk polymer composition was determined by matrix-assisted laser desorption/ionization time-of-flight (MALDI-TOF) mass spectrum analysis. MALDI-TOF analysis of the product according to Example 3 using an Applied Biosystems stainless steel sample plate and 3-indoleacrylic acid (IAA) or 2,5-dihydrobenzoic acid (2,5-DHB) as matrices provided the mass spectrum shown in FIG. 7 (portion of the spectrum between 5200 Da and 8000 Da is shown in the inset). This MALDI-TOF result confirmed that product according to Example 3 is a composition of polymers of formula (3a) generally having from about 4 to about 60 repeating units. FIG. 7 shows that the individual peaks each represent a polymer with repeating units of 134 atomic mass units. In particular, the parent molecular ion for each fraction from top to bottom in FIG. 7 has a mass to charge ratio (m/z) between 558 and 7700 Da. Representative peaks shown in FIG. 7 include, but are not limited to: 558.93, 692.59, 826.29, 960.06, 1093.76, 1227.45, 1361.08, 1494.73, 1628.39, 1761.96, 1895.59, 2162.87, 2430.14, 2696.54, 2964.38, 3364.14, 3765.36, 4165.97, 4565.15, 4963.63, 5367.30; and within the inset: 5495.09, 5637.66, 5773.34, 5903.60, 6038.95, 6170.94, 6308.06, 6433.03, 6580.91, 6701.36, 6838.62, 6960.89, 7092.04, 7219.46, and 7362.96.

Determination of Biological Activity

Compounds and compositions of the invention are active against HIV, HSV and *N. gonorrhoeae* in vitro. The compounds of the present invention prevent HIV transmission by dendritic cells, which are important target cells for primary HIV infection. The compounds and compositions retain anti-viral activity (HIV and HSV-2) in the presence of cervical secretions and across a wide pH range in vitro. The compounds and compositions inhibit hyaluronidase and acrosin, induce sperm acrosomal loss, and are contraceptive in a rabbit model.

Example 12

Prevention of HIV and HSV Infection and Synergism with Reverse Transcriptase Inhibitors Materials and Methods Microbicides. PPCM is synthesized by researchers at the Program for the Topical Prevention and Conception of Disease (TOPCAD) at University of Illinois Chicago (Chicago, Ill.). 0.4% and 4% PPCM gels (and the matched placebo gel) is provided by Yaso Biotechnologies, Inc. (Coppell, Tex.). PMPA (tenofovir) is obtained from Gilead Sciences, Inc. (Foster City, Calif.), and UC-781 is obtained from Biosyn, Inc. (Philadelphia, Pa.).

Cell and virus cultures. Cells and viruses are obtained from the AIDS reagent project, National Institute for Biological Standards and Control, Potters Bar, United Kingdom, unless stated otherwise. ME-180 cells, a cervical epithelial cell line (obtained from American Type Culture Collection, Manassas, Va.), and TZM-bl cells, a HeLa cell line stably expressing CD4 and CCR5 and used for quantitative analysis of HIV-1 with luciferase as a reporter, are cultured in Dulbecco's modified Eagle's medium (DMEM) supplemented with 10% fetal calf serum, 2 mM L-glutamine, 100 U/ml penicillin, and 100 µg/ml streptomycin (complete DMEM). Vero cells and the T-cell lines PM-1 and H9 are cultured in RPMI 1640 supplemented like DMEM (complete RPMI). Jurkat-Tat-CCR5 cells, a T-cell line which has been transfected with the HIV-1 tat gene and the CCR5 coreceptor, rendering it permissive to X4 and R5 viruses, are provided by Quentin Sattentau (Sir William Dunn School of Pathology, University of Oxford, Oxford, United Kingdom) and cultured in complete RPMI supplemented with 250 µg/ml hygromycin B (for Tat selection) and 500 µg/ml Geneticin (for CCR5 selection). Raji cells stably expressing DC-SIGN (Raji/DCSIGN cells) and negative-control cells are provided by V. N. Kewal Ramani (National Cancer Institute, Frederick, Md.) and are cultured in complete RPMI (supplemented with 500 µg/ml geneticin for the transfected cells). All cells are passaged every 3 to 4 days and cultured in a humidified incubator containing 5% $CO_2$. The primary HIV-1 isolates belonging to clades B and C, a gift from John P. Moore (Weill Medical College, Cornell University, New York, N.Y.). The laboratory-adapted HIV-1 strains HIV-1RF (X4-utilizing strain) and HIV-1BaL (R5-utilizing strain) are grown in PM-1 cells and stored at −180° C. after filtration through 0.2-_m filters (Millipore, Mass.).

Anti-HSV Murine Model. Five days prior to infection, mice are treated with 2 mg/ml Depo-Provera. On day 0, the mice are treated with 30 µl of 0.4% or 4% PPCM gel or a matched placebo gel 15 min prior to challenge with 20 µl of HSV-2 (G) (1×$10^5$ PFU) diluted in PBS or in pooled human seminal plasma obtained from males at low risk for STI. Mice are monitored for signs of disease for 14 days postinfection on a 0- to 4-point scale: 0, no apparent infection; 1, slight redness of the vagina; 2, moderate redness and swelling of the vagina and surrounding tissue; 3, severe redness, swelling, and hair loss of the genital and surrounding tissues; and 4, genital ulceration with severe redness, swelling, and hair loss of the genital and surrounding tissues. Mice reaching stage 4 genital disease or exhibiting neurologic signs (hind limb paralysis) are euthanized.

Luciferase assay for detection of HIV-1 infection. TZM-bl cells are exposed to 103 TCID50 of HIV-1 in the presence of various concentrations of PPCM alone or in combination with the reverse transcriptase (RT) inhibitors UC-781 and PMPA. Virus and drugs are left in culture for 48 h at 37° C.

and then removed by washing once with 200 μl PBS. Following cell lysis with luciferase cell culture lysis reagent (Promega, Southampton, United Kingdom), luciferase activity in lysates is determined.

Anti-HIV activity of PPCM in cell models. Cell-free HIV-1 (BaL or RF) is captured to 96-well plates coated with a monoclonal antibody against human HLA-DR. Unbound virus is removed by washing, and immobilized virus is treated with 100 μl of serial dilutions of PPCM for 1 h at 37° C. To assess direct virucidal activity, the compound is removed and the plates are washed four times with 200 μl PBS before addition of target cells ($4 \times 10^4$ Jurkat-Tat-CCR5 cells per well). Alternatively, cells are added without removal of compound or, to assess cell protection, Jurkat-Tat-CCR5 cells ($4 \times 10^4$ cells/well) are exposed to the same concentrations of compound in U-bottom 96-well plates and washed in the same way before transfer to plates with immobilized virus. Viral replication is assessed by measuring RT levels in culture supernatants at 7 days postinfection.

To evaluate the activity of PPCM against cell-associated HIV-1, PM-1 or H9 cells chronically infected with B clade isolate HIV-1RF, HIV-1IIIB, or HIV-1BaL or the clade C clinical isolate Za003/97 are treated with 200 μg/ml mitomycin C in complete medium for 1 h at 37° C. Infected cells are washed twice with 50 ml PBS, added to 96-well plates (500 cells/well), and incubated with various concentrations of PPCM for 1 h before addition of $4 \times 10^4$ Jurkat-Tat-CCR5 cells per well. Cocultures are incubated at 37° C. for 5 days and culture supernatants collected and stored at −20° C. prior to measurement of RT activity as before.

PPCM inhibition of HIV-1 infection in cell culture. PPCM can prevent infection of TZM-bl indicator cells by laboratory adapted and primary clade C and B HIV isolates. At a concentration of 100 μg/ml, a concentration that should be readily found in genital tract secretions following application of either a 0.4% or a 4% PPCM formulation, PPCM can completely block infection by all isolates tested, with no cytotoxicity at the dose concentration.

Combination studies. PPCM and RTIs are combined at 1:1 ratios in terms of 50% inhibitory concentrations (IC50) and treated as a single drug that is used at a range of dilutions in the viral inhibition assay (luciferase assay). To determine the ratios of compound that should be used in these studies, IC50 values are determined following exposure of TZM-bl cells to each viral isolate in the presence of single drugs for 48 h. The PPCM/PMPA ratios are 1:13.213 and 1:0.015 for HIV-1RF and HIV-1BaL, respectively, whereas the PPCM/UC-781 ratios are 1:0.055 and 1:0.015 for the X4 and R5 viruses, respectively. In parallel, single drugs are tested at the same concentrations.

PPCM can protect mice challenged vaginally with HSV-2. Female Balb/c mice are pretreated with 30 ul of either 0.4% PPCM, 4% PPCM or matched placebo gel and then 15 minutes later inoculated with 20 ul of $1 \times 10^5$ (LD90) dose of HSV-2G diluted in either PBS or semen. Results showing survival are pooled from 4 independent experiments (n=5-10 mice/group/experiment). 4% PPCM can significantly protect the mice when virus is delivered in both PBS and semen (e.g., p<0.0001 and p<0.0004, respectively, log rank test). The 0.4% PPCM can afford significant protection (e.g., p<0.002).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A polymer comprising a distribution of compounds of formula (I)

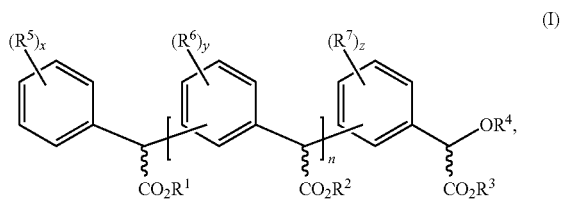

or a pharmaceutically acceptable salt, ester, amide, or prodrug form thereof, wherein $R^1$, $R^2$, and $R^3$ are each independently selected from the group consisting of hydrogen, alkyl, alkenyl, alkynyl, cycloalkyl, heterocycle, heteroaryl, aryl, and counterion;

$R^4$ is independently selected from the group consisting of hydrogen, alkyl, alkenyl, alkynyl, cycloalkyl, heterocycle, heteroaryl, and aryl;

$R^5$, $R^6$, and $R^7$ are each independently selected from the group consisting of alkyl, alkoxy, and halogen;

n is an integer greater than zero;

x, y, and z are each an integer independently selected from the group consisting of 0, 1, 2, 3, and 4;

and wherein the polymer is produced by a process comprising:

cooling a strong acid to a temperature below 0° C. in the absence of solvent;

adding mandelic acid or a mandelic acid derivative to the strong acid; and isolating the polymer.

2. The polymer of claim 1, wherein the strong acid is cooled to a temperature below −10° C.

3. The polymer of claim 1, wherein the strong acid is cooled to a temperature below −30° C.

4. The polymer of claim 1, wherein the mandelic acid or mandelic acid derivative is added over a period of about 30 minutes.

5. The polymer of claim 1, wherein the reaction mixture is maintained at a temperature ranging from about −35° C. to about −30° C. for a period of about 1 hour.

6. The polymer of claim 1, wherein the strong acid is concentrated sulfuric acid.

7. The polymer of claim 1, wherein the process is conducted under neat reaction conditions.

8. The polymer of claim 1, wherein the compounds have a structure of formula (3a):

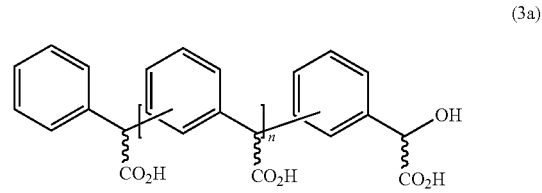

and wherein the isolated polymer has a melting point (mp) of 205-206° C. and demonstrates NMR peaks as follows: $^1$H NMR (DMSO-d$_6$): δ 7.35-7.02 (m), 5.23 (br, s), 5.15-4.75 (m), 3.41 (br, s), and $^{13}$C NMR (DMSO-d$_6$): δ 174.09, 140.23, 139.72, 138.85, 138.25, 129.38, 127.96, 56.76.

9. The polymer of claim 1, wherein the compounds have a structure of formula (5a):

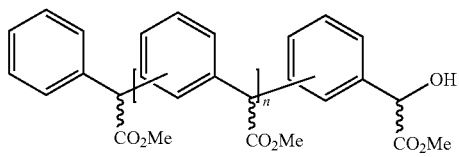

(5a)

and wherein the isolated polymer has a melting point (mp) of 125-126° C. and demonstrates NMR peaks as follows: $^1$H NMR (DMSO-d$_6$): δ 7.26-6.96 (m), 5.30 (s), 5.05-4.80 (m), 3.76-3.46 (m).

10. The polymer of claim 1, wherein the compounds have a structure of formula (7a):

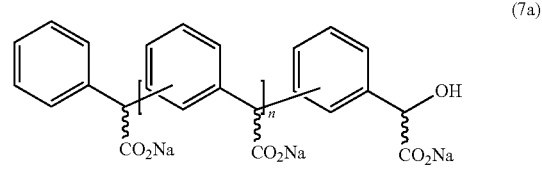

(7a)

and wherein the isolated polymer has a melting point (mp) of 320-321° C.

11. A method for protecting an individual from contracting a sexually transmitted disease through contact with a bodily fluid, said method comprising applying to the body or portion of the body of the individual an effective amount of a protective agent, wherein the protective agent comprises a compound according to claim 1.

12. A method of reducing the risk of transmission of a sexually transmitted pathogen to a human subject, comprising contacting the pathogen or cells susceptible to infection by the pathogen with an effective amount of a compound according to claim 1, thereby reducing the risk of transmission of the pathogen.

13. The method of claim 11, wherein the sexually transmitted disease is HIV/AIDS.

* * * * *

UNITED STATES PATENT AND TRADEMARK OFFICE
CERTIFICATE OF CORRECTION

PATENT NO. : 9,527,793 B2
APPLICATION NO. : 14/361993
DATED : December 27, 2016
INVENTOR(S) : Robert A. Anderson et al.

Page 1 of 1

It is certified that error appears in the above-identified patent and that said Letters Patent is hereby corrected as shown below:

In the Specification

Column 1, Line 15, delete "This invention was made with government support under contract nos. R43 AI084225-01A2 and P01 HD041763-03, awarded by the National Institutes of Health. The government has certain rights in the invention." and insert -- This invention was made with government support under grant nos. R43 AI084225 and P01 HD041763, awarded by the National Institutes of Health. The government has certain rights in the invention. --

Signed and Sealed this
Second Day of January, 2018

Joseph Matal
*Performing the Functions and Duties of the
Under Secretary of Commerce for Intellectual Property and
Director of the United States Patent and Trademark Office*